United States Patent [19]
Dean

[11] Patent Number: 5,180,816
[45] Date of Patent: Jan. 19, 1993

[54] ONE VIAL METHOD FOR LABELING PROTEIN/LINKER CONJUGATES WITH TECHNETIUM-99M

[75] Inventor: Richard T. Dean, Downingtown, Pa.

[73] Assignee: Centocor, Malvern, Pa.

[21] Appl. No.: 235,908

[22] Filed: Aug. 24, 1988

[51] Int. Cl.$^5$ .................. C07K 3/08; A61K 43/00; G01N 33/53
[52] U.S. Cl. .................. 530/404; 424/1.1; 424/9; 436/547; 436/512; 548/548
[58] Field of Search .............. 424/1.1, 9; 436/547, 436/512; 206/569; 548/548; 530/404

[56] References Cited

U.S. PATENT DOCUMENTS

| | | | |
|---|---|---|---|
| 4,305,922 | 12/1981 | Rhodes | 424/1 |
| 4,659,839 | 4/1987 | Nicolotti et al. | 548/546 |
| 4,671,958 | 6/1987 | Rodwell et al. | 424/85 |
| 4,775,638 | 10/1988 | Haisma | 436/547 |
| 4,861,869 | 8/1989 | Nicolotti et al. | 530/402 |

FOREIGN PATENT DOCUMENTS 0173629 3/1986 European Pat. Off. .
188256 7/1986 European Pat. Off. .

OTHER PUBLICATIONS

Khaw, et al., *Science*, 209, 295–297 (1980).
Krejcarek et al., *Biochem. Biophys. Res. Comm.*, 77, 581–585 (1977).
Childs, et al., *J. Nucl. Med.*, 26, 293 (1985).
Fritzberg, et al., *J. Nucl. Med., 27, 957–958 (1986)*.
Eary, et al., *J. Nucl. Med.*, 28, 650–651 (1987).
Quadri, et al., *J. Nucl. Med.*, 27, 959 (1986).
Yokoyama, et al., *J. Nucl. Med.*, 28, 572 (1987).
Paik, et al., *J. Nucl. Med.*, 29, 889 (1988).
Paik, et al., *J. Nucl. Med.*, 28, 602 (1988).
Deshpande, et al., *J. Nucl. Med.*, 29, 922–923 (1988).

*Primary Examiner*—Carolyn S. Elmore
*Assistant Examiner*—B. Bembenick
*Attorney, Agent, or Firm*—Woodcock Washburn Kurtz Mackiewicz & Norris

[57] ABSTRACT

A one vial method for labeling a protein, such as an antibody or antibody fragment, with a radiometal such as Tc-99m or a rhenium isotope, is disclosed. The method comprises contacting in a single vial a mixture comprised of a reducing agent and a protein molecule covalently bound to a sulfhydryl containing bifunctional coupling agent with Tc or Re in an oxidized state. A one vial kit for labeling a protein with Tc or Re is also disclosed.

46 Claims, No Drawings

ONE VIAL METHOD FOR LABELING PROTEIN/LINKER CONJUGATES WITH TECHNETIUM-99M

BACKGROUND OF THE INVENTION

1. Field of the Invention

This invention relates to the field of immunodiagnostics and radioimmunotherapy and, more particularly, to methods for labeling antibodies, fragments thereof and peptides with metal ions.

2. Background of the Invention

Proteins have been labeled with various radiometals and other radioisotopic elements for use in immunodiagnostic and immunotherapeutic procedures. Some radiometals have superior properties for use in these techniques. Technetium-99m is an ideal radionuclide for scintigraphic imaging because of its nuclear properties. It has a single photon energy of 140 KeV, a half-life of about 6 hours, and it is readily available from a $^{99}$Mo-$^{99m}$Tc generator.

Two general approaches have been taken to label proteins such as antibodies with radiometals. The first is the direct labeling method by which the radiometal is bound to the protein molecule itself. The second is the indirect labeling method in which a complexing agent is coupled to the protein and the radiometal is attached to the protein via the complexing agent.

Rhodes discloses a method of direct labeling of protein with technetium-99m which involves ligand solid phase exchange. See U.S. Pat. No. 4,305,922. According to the method of Rhodes, pertechnetate is reduced to technetium IV and then applied onto a Sephadex ® column. The reduced technetium-99m binds to the Sephadex ® material. A solution of the protein to be labeled is poured onto the top of the Sephadex column where it is allowed to remain so that ligand exchange occurs. As a result, the technetium-99m is transferred preferentially from the Sephadex ® material to the protein. The protein may be pretreated with stannous chloride (a procedure called "pretinning") to enhance transfer of the radiometal to the protein. See U.S. Pat. No. 4,424,200.

Various attempts have been made to label proteins with radiometals by the indirect approach. In one such approach, a chelating agent such as diethylenetriaminepentaacetic acid (DTPA) is conjugated onto the protein and then the metal ion is labeled onto the chelating agent attached to the protein molecule. For example, Khaw et al., *Science* 209: 295-297 (1980) discloses antibodies to cardiac myosin labeled with indium-111 via DTPA and use of the labeled antibodies to image for myocardial infarction. See also, Krejcarek et al., *Biochem. Biophys. Res. Commun.* 77: 581-585 (1977); Childs, R. L. and Hnatowich, D. J., *J. Nucl. Med.* 26: 293 (1985). In a more recent approach, Fritzberg et al. describe the use of particular diamidodithiol and diaminodithiol groups, as a chelating agents. Fritzberg et al, *J. Nucl. Med.* 27: 957 (1986); European Patent Application 86100360.6.

Various degrees of success have been achieved with both the direct and indirect methods of labeling proteins with radiometals; however, the labeled product is often unstable in vivo. Also, techniques for purifying the labeled product before use are often required. Methods for labeling proteins can be further complicated when radiometals such as technetium (Tc) or rhenium (Re), desirable because of their nuclear properties and ready availability, are used. Such radiometal are available in oxidized states and must be subjected to reducing conditions before labeling. Since such radiometals have relatively short half-lives, time-consuming labeling procedures are obviously disadvantageous.

Clearly, there are numerous obstacles to a simple and efficient method for radiolabeling proteins, one which can be conveniently, rapidly and reliably performed by a clinician or technician prior to the use of the labeled protein as a therapeutic or diagnostic tool.

SUMMARY OF THE INVENTION

A simple, rapid and efficient one vial method for labeling a protein molecule with a radiometal such as Tc or Re has now been found. The method of this invention comprises contacting in a single vial, under non-oxidizing conditions, a mixture comprised of a reducing agent and a protein molecule covalently bound to a sulfhydryl containing bifunctional coupling agent with Tc or Re in an oxidized state. Thus, the reduction of the oxidized form of the radiometal and the radiolabeling reaction itself (i.e., the coupling of the radioisotope to protein) are achieved in a single vial. This invention further relates to a kit which can be used to label a protein with Tc or Re. The kit comprises a single vial containing a mixture comprised of protein covalently bound to a sulfhydryl containing bifunctional coupling agent and a reducing agent under non-oxidizing conditions. To this vial is added the Tc or Re in oxidized state to effect a quantitative transfer of the radiometal to the protein.

The labeled proteins prepared using the method or kit of this invention can be injected into the patient without purification. The labeled protein molecules, may be extremely useful as diagnostic agents, for example, for immunoscintigraphy of tumor, myocardial infarction, thromboses, atherosclerotic plaques or bacterial abscesses. The method is simple, efficient, and reproducible and it minimizes the safety hazards to persons performing the radiolabeling. The method of this invention is particularly suited for labeling antibodies (polyclonal and monoclonal) and peptides for diagnosis and therapy. Peptides and antibodies can be labeled by this method to a high specific activity with minimal loss of activity or immunoreactivity.

There are several advantages arising from use of the present one vial method over methods using two vials and other known methods for labeling with radiometals such as technetium-99m. For example, rapid labeling at ambient conditions is possible. Labeling yields greater than 90% may be achieved in 5-15 minutes at ambient temperature without heating. The clinical advantages of near instantaneous preparation of a diagnostic agent can be substantial. Also, the stability of the lyophilized formulation of the single vial method should be superior to the comparable formulation employed in a two vial method.

DETAILED DESCRIPTION OF THE INVENTION

Antibodies, Antibody Fragments or Peptides

As used herein, the expression "protein molecule" refers 5 to polypeptides having two or more amino acids. In preferred embodiments, the method of this invention is used to label whole antibodies (e.g., IgG), antibody fragments (e.g., Fab') or peptides. For most immunodiagnostic and immunotherapeutic procedures, antibody fragments are preferred reagents. Antibody fragments have a number of advantages over whole antibodies including, in general, more rapid distribution and accumulation at target site and less immunogenicity.

Fab' fragments are monovalent binding antibody fragments which contain free sulfhydryl groups (when maintained under nonoxidizing conditions). Fv fragments could also be prepared and these fragments can be labelled efficiently by the method of this invention. In addition peptides, such as TPA, can be labelled by the present method.

Fab' fragments can be prepared from whole antibodies as follows: an antibody molecule is first treated with an endopeptidase such as pepsin to remove the Fc portion of the antibody molecule. The resultant F(ab')$_2$ fragment is treated with a reducing agent such as DTT or cysteine to reduce disulfide bonds present on the F(ab')$_2$ fragment resulting in exposed sulfhydryl groups on the molecules and thereby also producing two Fab' molecules for each antibody molecule.

A sulfhydryl containing bifunctional coupling agent is covalently bound to the protein which agent serves to couple the protein and the radiometal. Methods for effecting such covalent bonding are well known to those skilled in the art. For example, an active ester (e.g., N-hydroxysuccinimide ester) or an isothiocyanate derivative of the coupling agent may be used to bind the agent to amine functions on the protein; a 2-iodoacetyl or maleimido derivative of the coupling agent may be used to bind the agent to sulfhydryl groups of the protein; a hydrazide derivative of the agent may be used to bind the agent to oxidized carbohydrate groups on the protein; or a carbodiimide reagent such as 1-ethyl-3-(3-diaminopropyl)carbodiimide may be used to bind an amino group of the coupling agent to a carboxyl group on the protein. Whole antibodies (e.g. IgG) and peptides naturally occur with amine and carboxyl groups. Whole antibodies can be reduced with the reducing agent dithiothreitol (DTT) for example, to produce sulfhydryl containing antibodies. Carbohydrate groups on the antibody can be oxidized with sodium periodate or enzymatically using, for example, glucose oxidase.

Fab' fragments are especially suited for labeling by the procedure. Under nonoxidizing conditions, these fragments contain free sulfhydryl groups (as they are produced by reduction of disulfide bridges present in F(ab')$_2$ fragments). For most radioimmunodiagnostic techniques, antibody fragments such as Fab' fragments are preferred and thus, the labeling procedure of this invention is particularly suited for preparing radiopharmaceuticals for these techniques.

Sulfhydryl Containing Bifunctional Coupling Agents

The sulfhydryl containing bifunctional coupling agents useful in the method of the invention are molecules containing an electrophilic or nucleophilic portion capable of forming a stable bond with a protein functionality, as described above, and a complexing portion containing at least one sulfhydryl group which portion is capable of complexing a desired radionuclide. Since the sulfhydryl group in the coupling agent may be incompatible with a sulfhydryl-selective electrophile which is part of the same coupling agent, the sulfhydryl group may be suitably protected from reaction with the electrophilic moiety during attachment of the bifunctional coupling agent to the protein substrate.

Certain preferred coupling agents of this invention are selectively bound to the protein through sulfhydryl sites and can be represented by the general formula E—L—C, wherein E is a sulfhydryl selective electrophile, L is an organic linking radical and C is a radionuclide chelator containing at least one protected thiol. Sulfhydryl sites on biologically functional proteins such as antibodies are usually distal to the antigen binding sites. When sulfhydryl-selective coupling agents are utilized, the accompanying radionuclide chelator is removed from the antigen binding region of that antibody, reducing the likelihood of interference of the chelator with antibody-antigen bonding. Sulfhydryl-selective coupling agents which are useful in the method of this invention, and methods of preparing them, are disclosed in copending and co-assigned patent applications U.S. Ser. No. 199,931(pending), filed on Jun. 15, 1988, and U.S. Ser. No. 07/235,999 (U.S. Pat. No. 5,144,043), filed simultaneously herewith. The disclosures of both of these applications are herein incorporated by reference.

The sulfhydryl-selective electrophile, E, is that portion of the bifunctional coupling agent which forms a bond with a sulfhydryl moiety on the protein to be labelled. Suitable electrophiles include any functionality capable of forming a stable bond with a protein sulfhydryl in the presence of other reactive groups normally found on proteins. Examples of sulfhydryl-selective electrophiles include those in the group consisting of haloalkyl, sulfonate ester, maleimide and aziridine. Preferably, the sulfhydryl selective electrophile is selected from the group consisting of ClCH$_2$CONH—, BrCH$_2$CONH—, ICH$_2$CONH— and N-substituted maleimide.

The chelator, C, is that portion of the bifunctional coupling agent which forms a bond with the radionuclide, and this moiety contains at least one protected thio group. The thiol-containing chelating moiety is suitably protected from reaction with the electrophilic moiety during attachment of the bifunctional coupling agent to the protein substrate. As used herein, the expression "protected thiol" refers to a thiol-containing moiety wherein the thiol group(s) is(are) reversibly derivatized such that the thiol(s) is(are) rendered unreactive. After attachment to the protein substrate the chelating moiety can be deprotected to unmask the chelating functionality for radionuclide binding.

Groups suitable for protecting the thiol from reaction are organic and inorganic groups which can be readily removed under mild conditions (described in more detail hereinafter) to regenerate the free thiol in the presence of the protein without substantially altering the activity of the protein. In preferred embodiments of the invention, the thiol protecting group is selected from the group consisting of thiol esters, disulfides and Michael-addition products. More preferably the protecting group is a thiol ester.

Preferably the chelator is selected from those of the formula:

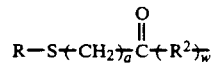

and

-continued

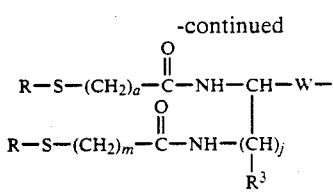

wherein a, j and m are independently an integer of 1 to 3 inclusive, and most preferably 1; R is $R^1CO-$ or $R^1S-$, wherein $R^1$ is methyl, optionally substituted lower alkyl, and optionally substituted aryl, and most preferably R is $R^1CO-$ wherein $R^1$ is phenyl or phenyl substituted with a functional group; each $R^2$ is independently selected from the units

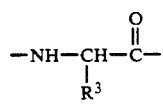

and

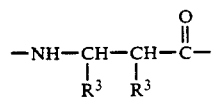

and W is an integer from 3 to 6 inclusive, and preferably $R^2$ is $NHCH(R^3)CO-$ units and W is 3; W is a carbonyl group or $-CHR^3-$; each $R^3$ is independently selected from hydrogen, optionally substituted lower alkyl, optionally substituted aryl, and most preferably $R^3$ is hydrogen or hydroxymethyl. The term "alkyl" as used herein includes branched and straight chain alkyl groups, and "lower alkyl" refers to such groups having up to six carbon atoms. The term "optionally substituted" as used herein refers to optional substitution with functional groups, such as but not limited to alkoxy groups, alkyl groups, aryl groups, hydroxy groups and carboxy groups, which will not interfere with the desired coupling and labelling reactions. Generally speaking, such functional groups are unreactive to reaction with mercaptans, sulfides, amines and alkylating agents.

The organic linking radical, L, has at least two valencies for joining the electrophilic moiety E and the chelating moiety C. Preferred organic linking radicals are selected from the group consisting of optionally substituted alkyl, optionally substituted alkyl containing heteroatom substituents for carbon (e.g., in which a carbon in the aliphatic chain is replaced with a heteroatom such as N, O or S), and optionally substituted aryl groups. Examples of preferred organic linking radicals are $-CONHCH_2CH_2-$, $-CH_2C_6H_4-$, $-NHCH_2CH_2-$ and $-CONHCH(CO_2H)CH_2CH_2CH_2CH_2-$.

The organic linking radical preferably contains one or more cleavable sites, thus enhancing clearance of the radiometal from non-target tissue. As used herein, the expression "cleavable site" refers to a chemical bond in the linking radical, the breaking of which bond serves to dissociate the radiometal in chelated form from the labelled protein, which bond is known to have an appreciable rate of dissociation by metabolism in an organ. Such dissociation should preferably occur at a rate of at least about 50% within the half-life of the radiometal.

The cleavable site can be part of the organic linking 5 radical or can form one of the bonds joining the organic linking radical to the chelating moiety and/or the electrophilic moiety. Most preferably, the cleavable site is an alkyl ester, an ester of an aryl alcohol or an aryl ester of an alkyl alcohol. Preferred organic linking radicals containing cleavable sites are selected 0 from those of the formula:

$$-X-(CH_2)_b-(OCH_2CH_2)_c-(Y)_q-(CH_2)_d-(OCH_2CH_2)_e-$$

wherein b is an integer from 0 to 6, preferably 2; d and e are independently integers from 0 to 5 inclusive, and preferably 2; c is an integer of from 0 to 5 inclusive, and preferably 1; q is 0 or 1; X is selected from the group consisting of $-NH-$, $-O-$ or $-S-$, and preferably $-O-$; Y is selected from the group consisting of $-CH_2COO-$, $-OOCCH_2-$, $-CH_2CONH-$, $-OCH_2COO-$, $-NHCOCH_2-$, and $-OOCCH_2O-$ and is preferably $-OCH_2COO-$; provided that, when X is other than $-O-$, then q is 1 and Y is other than $-CH_2CONH-$ or $-NHCOCH_2-$.

Preferred bifunctional coupling agents of the invention are represented by the following formulae:

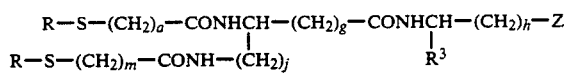

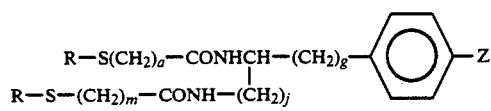

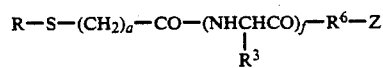

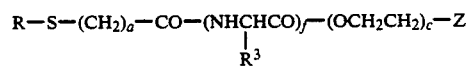

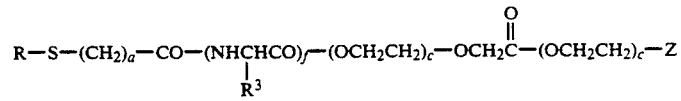

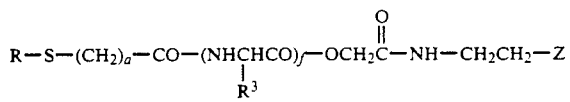

wherein a, m and j are independently integers from 1 to 3 inclusive; c is an integer from 1 to 7 inclusive; g and h are independently integers from 1 to 5 inclusive; f is an integer from 3 to 6 inclusive; R is $R^1CO-$ or $R^1S-$, wherein $R^1$ is selected from optionally substituted lower alkyl nd optionally substituted aryl; $R^3$ is selected from hydrogen, optionally substituted lower alkyl, and optionally substituted aryl; $R^6$ is a divalent, optionally substituted alkyl radical of from 1-6 carbon atoms; and z is selected from $ClCH_2CONH-$, $BrCH_2CONH-$, $ICH_2CONH-$ or N-substituted maleimide.

Specifically preferred bifunctional coupling agents of this invention are those of the formulae:

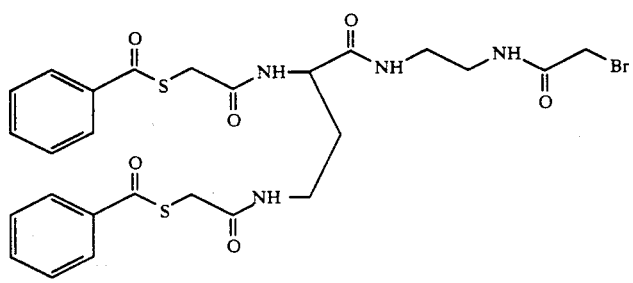

Compound I

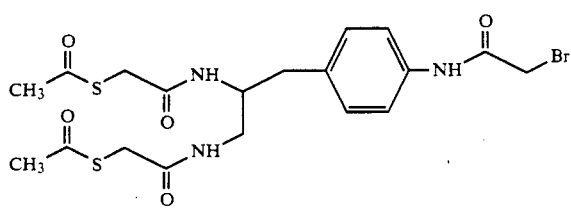

Compound II

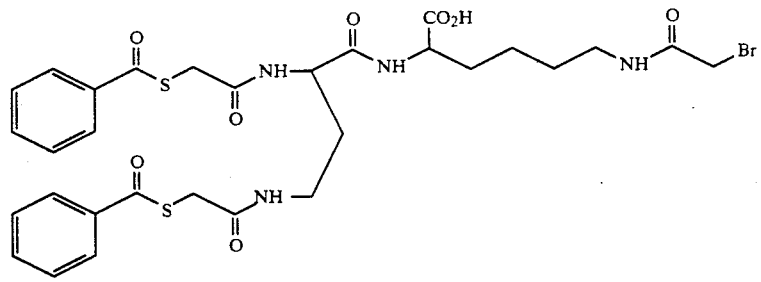

Compound III

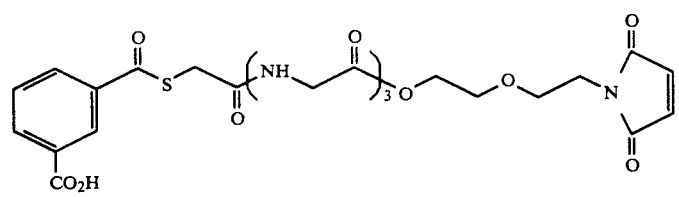

Compound IV

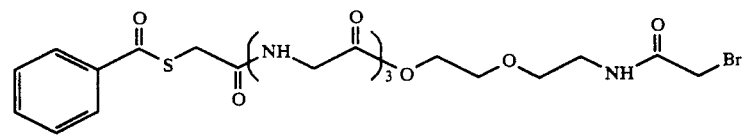

Compound V

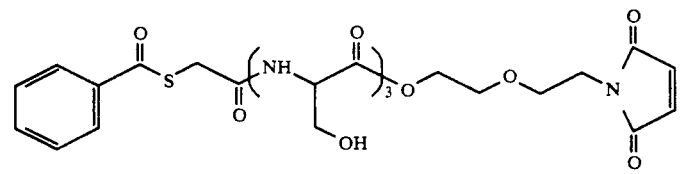

Compound VI

Compound VII
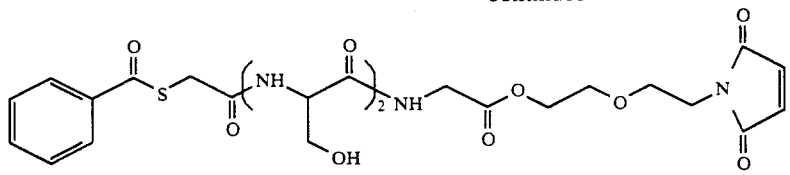
Compound VIII
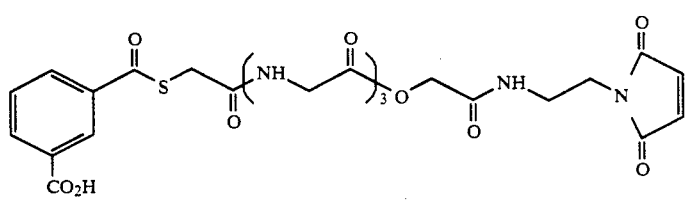
Compound IX
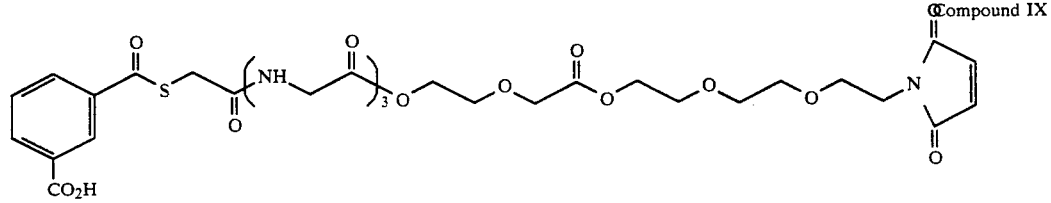
Compound X
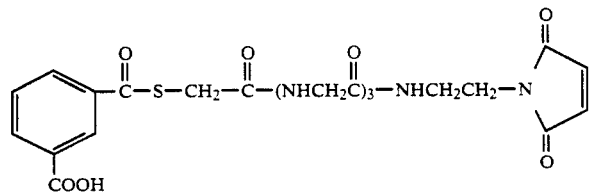
Compound I can be prepared according to the following scheme:
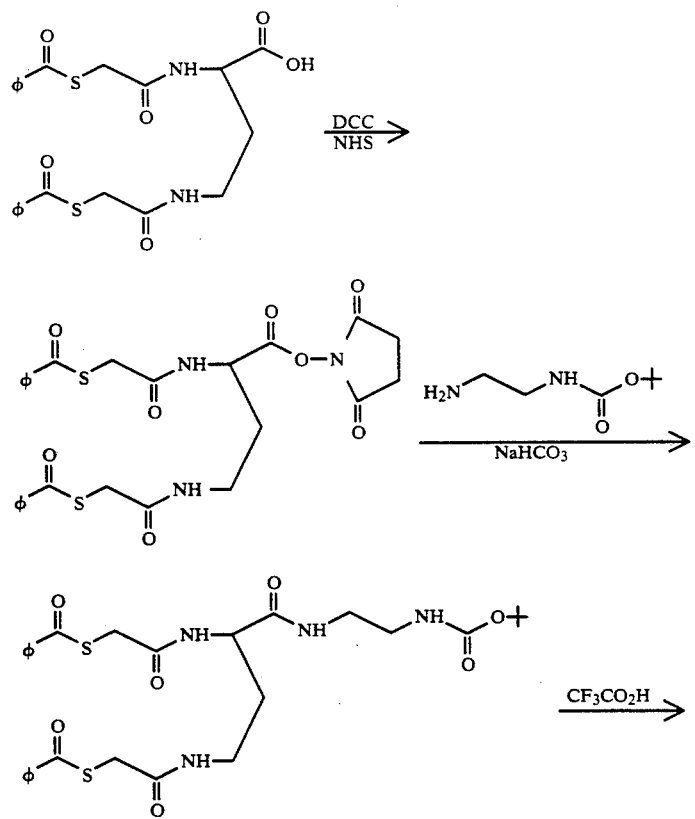

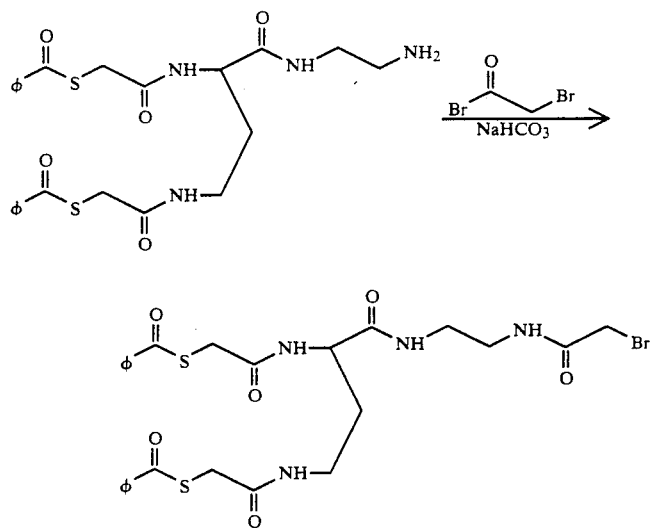
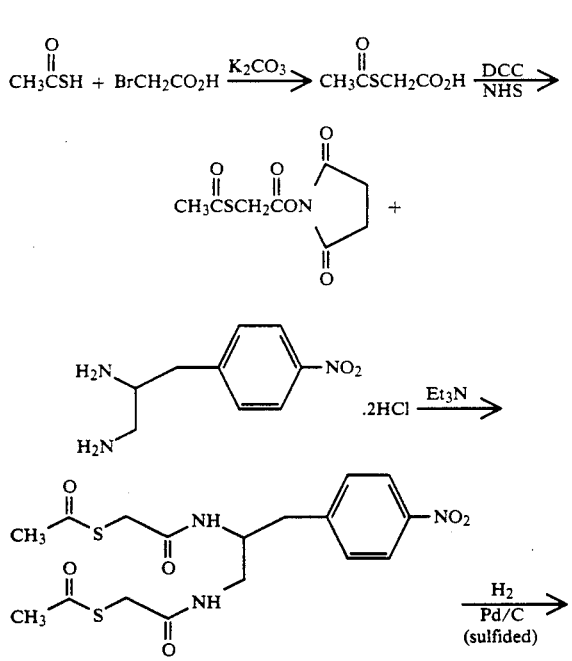
Compound II can be prepared according to the following scheme:
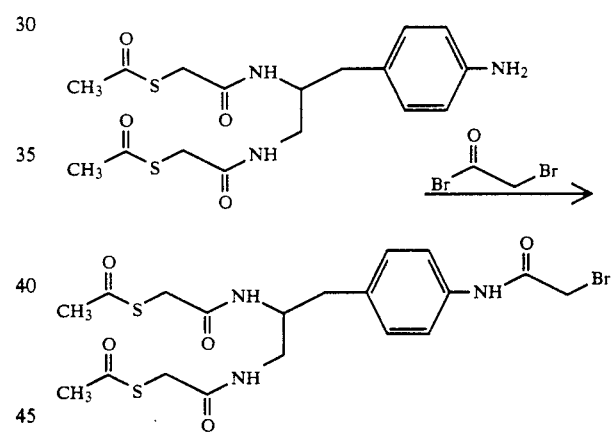
Compound III can be prepared according to the following scheme:
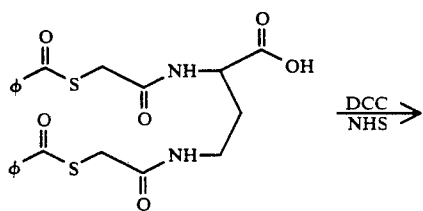

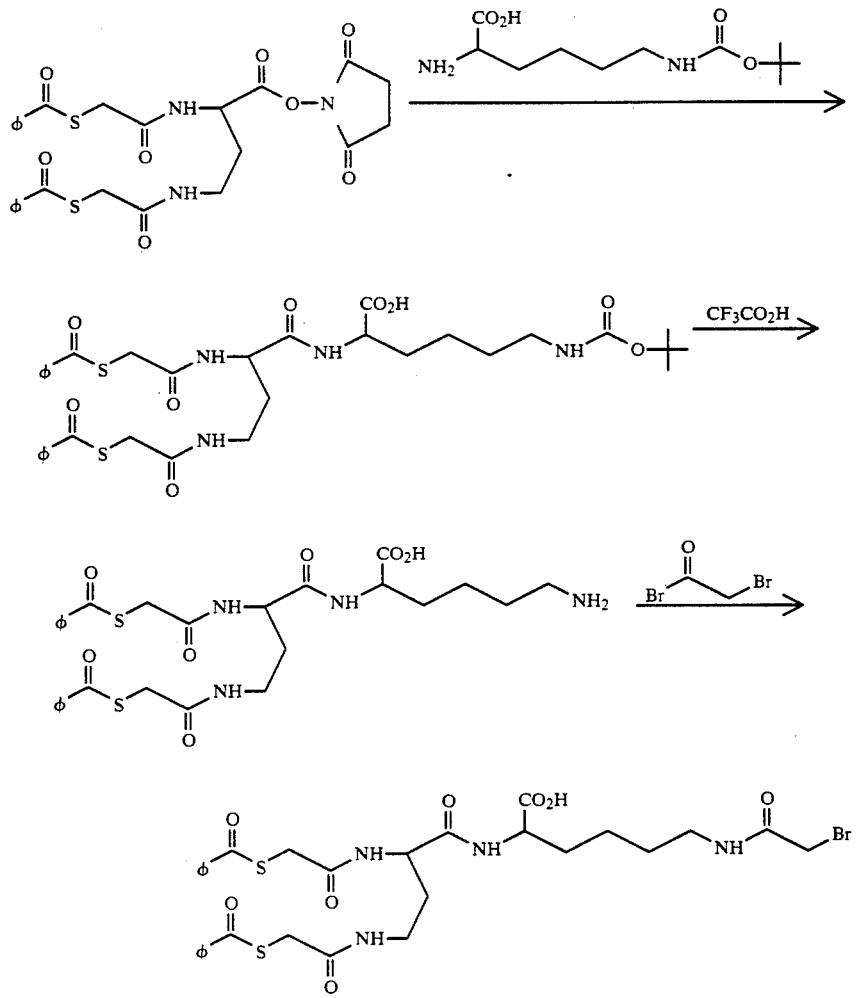
Compound IV can be prepared according to the following scheme:
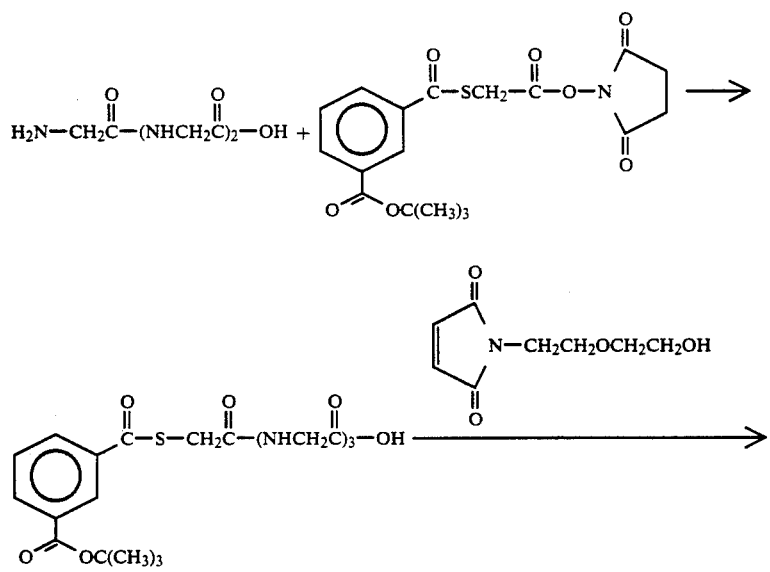

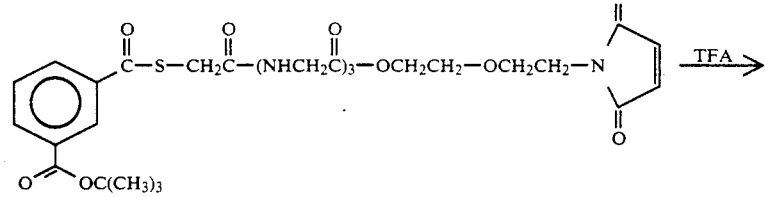
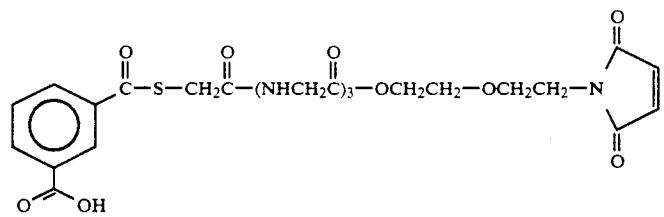
Compound V can be prepared according to the following scheme:
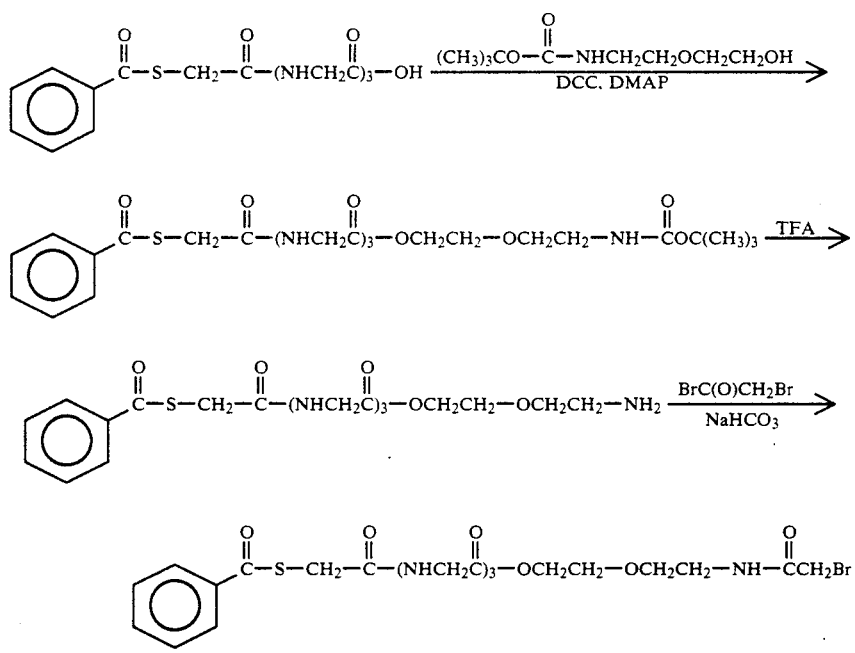
Compound VI can be prepared according to the following scheme:
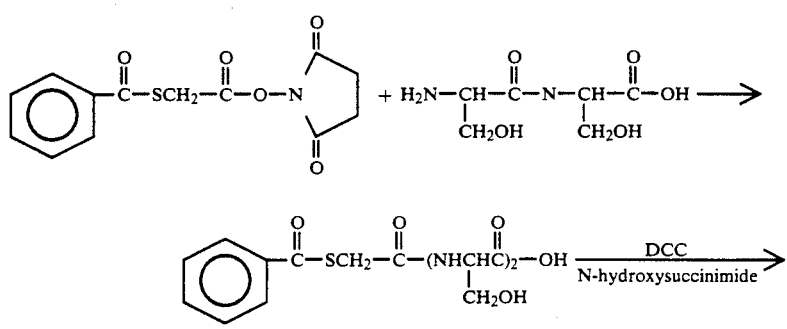

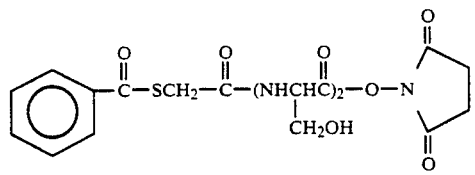
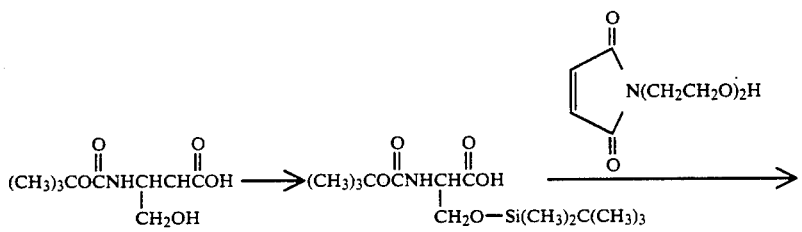
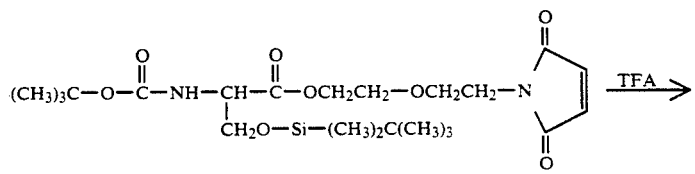
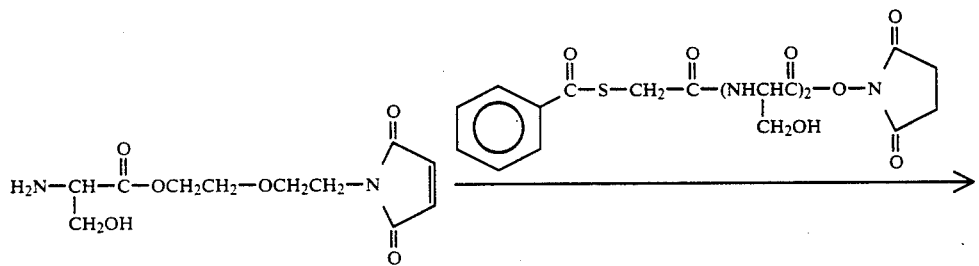
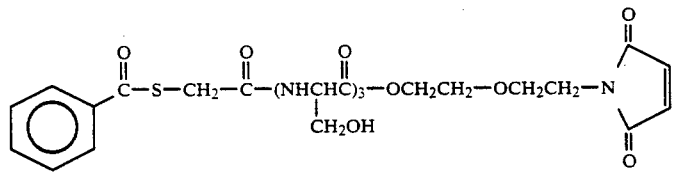
Compound VII can be prepared according to the following scheme:
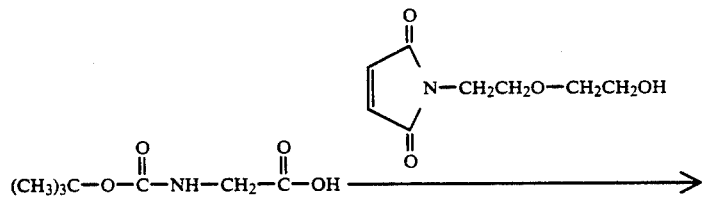
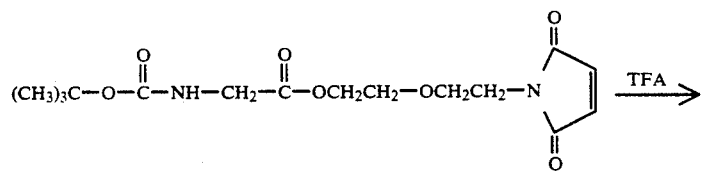

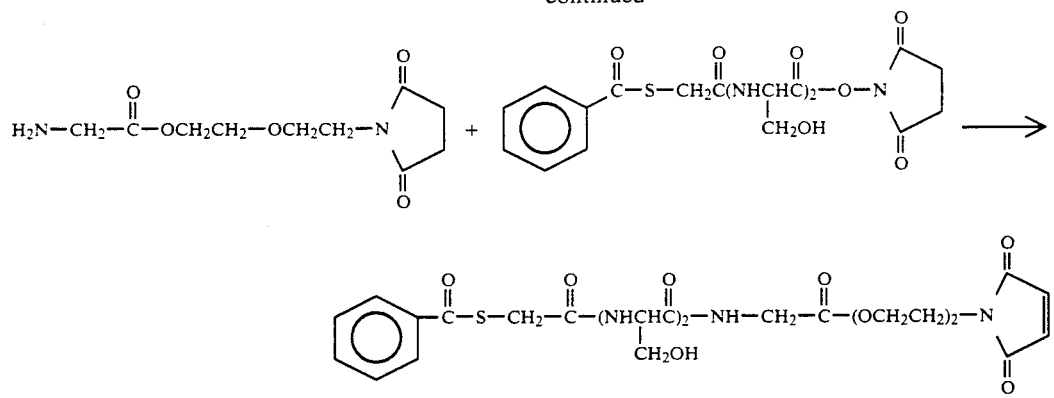
Compound VIII can be prepared according to the following scheme:
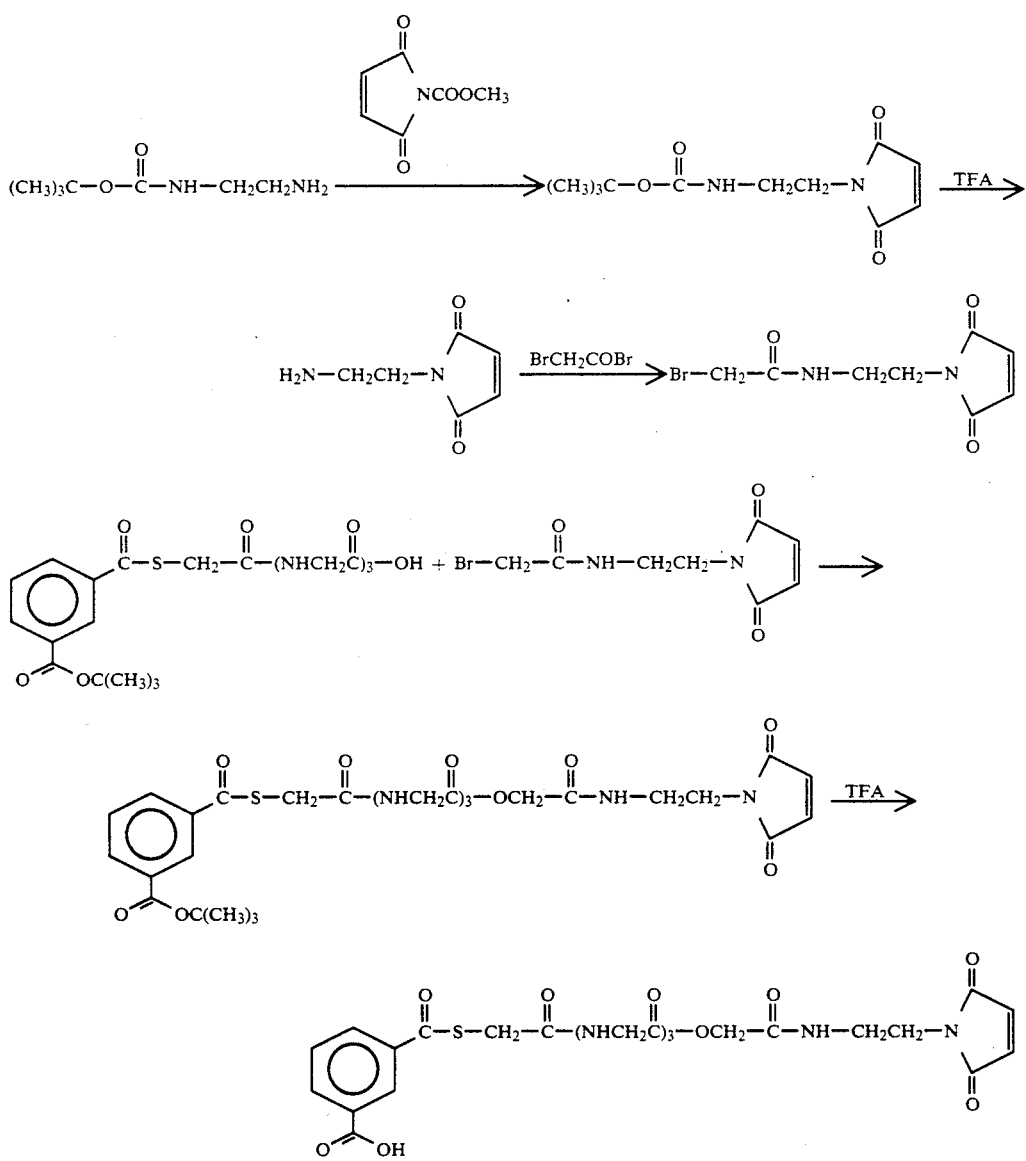
Compound IX can be prepared according to the following scheme:

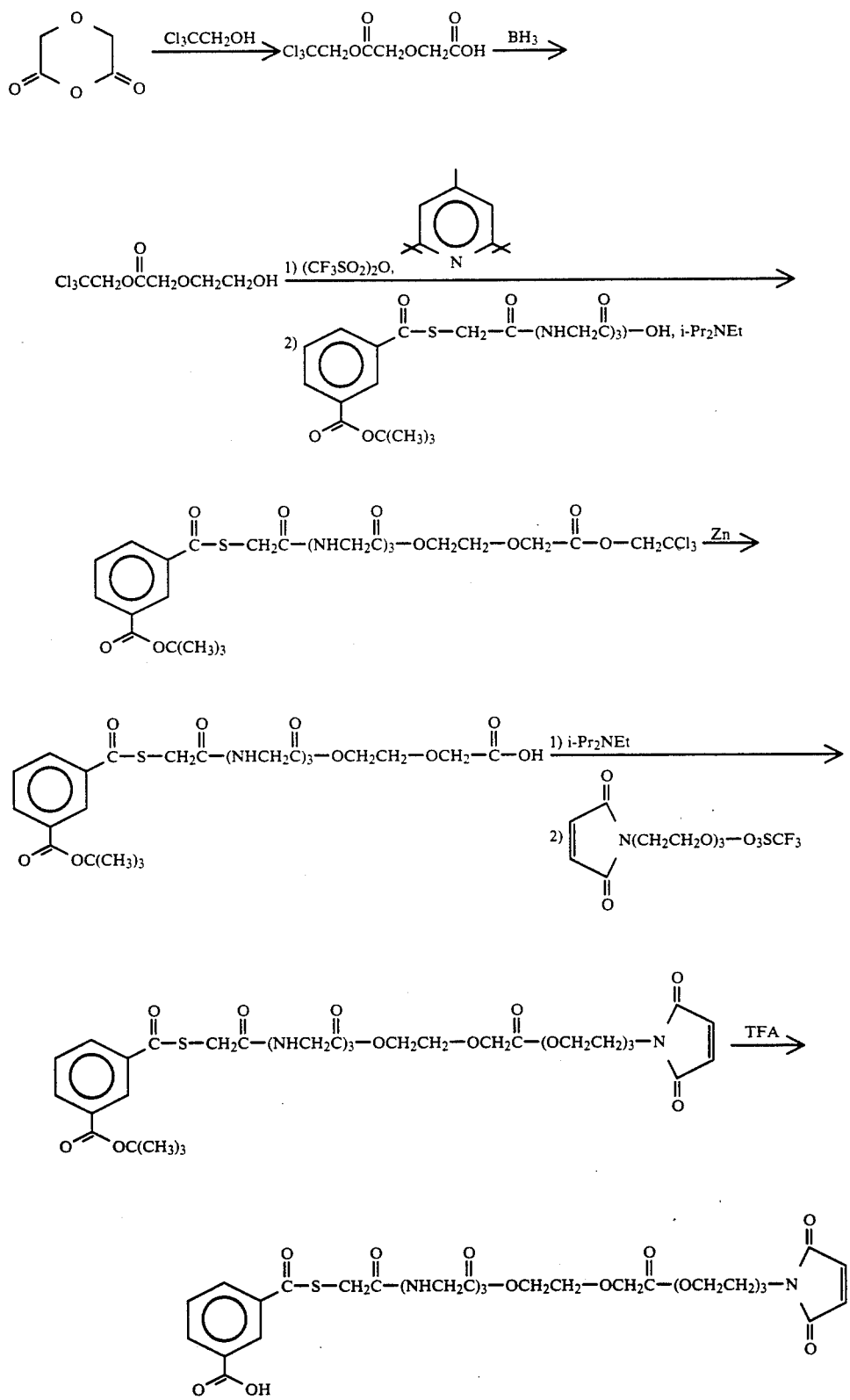
Compound X can be prepared according to the following scheme:

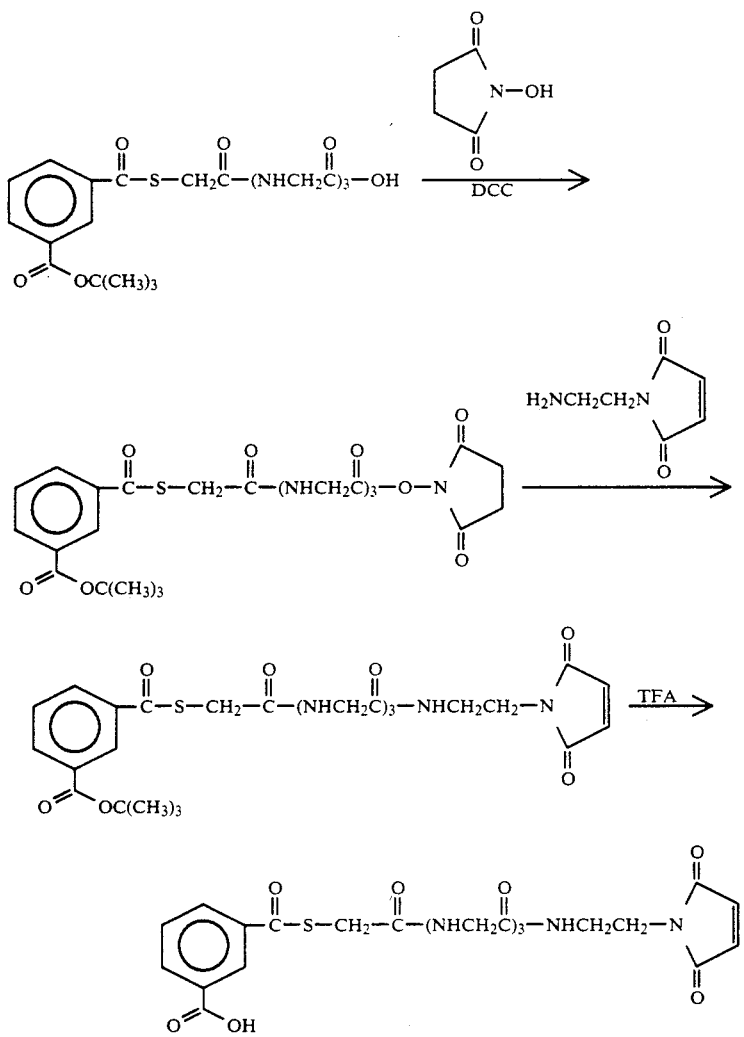

Water Soluble Ligands

The "one-vial" mixture of protein-coupling agent and reducing agent may preferably further contain a water soluble transfer ligand which complexes with the reduced radionuclide. In general, the transfer ligands useful in preferred embodiments of the present method are water soluble (or can be made water soluble) chelators which are capable of complexing technetium-99m or any of the rhenium radioisotopes in the reduced state to form a stable metal ion/ligand couples. The complex is further capable of exchanging the technetium-99m or rhenium with a sulfhydryl containing antibody or antibody fragment. Examples of suitable transfer ligands include DTPA, EDTA, di-, tri- or poly-alkylphosphonates, pyrophosphate or glycine and its derivatives.

Additional transfer ligands which can be used in the labeling method of this invention are represented by compounds (including physiologically acceptable salts thereof) having the general formula:

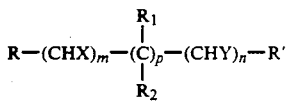

where
X and Y are OH or $NH_2$;
R and R' are independently H, COOH, or $CH_2OH$ or R and R' taken together can form a ring or bi- or multidentate ligand;
m and n are 0–10, such that m+n is at least 2;
$R_1$ and $R_2$ are independently H, optionally substituted lower alkyl, aryl and lower alkylaryl; and
p is 0 or 1 provided that, when p is 1, m and n independently are at least 1.

Some of the preferred water soluble ligands for use in the method are presented by the formula:

where
R and R' are COOH or $CH_2OH$, and n is an integer from 2 to 10 inclusive.

Among the ligands represented by this formula, polyhydroxydicarboxylic acids having a molecular weight of less than about 10,000 daltons are most preferred. Some specific examples of these types of ligands are D-glucaric acid, glucoheptonic acid, tartaric acid, galactaric acid, arabonic acid, and salts thereof.

The particularly preferred ligand for use in this method is D-glucaric acid. D-glucaric acid quickly and stably complexes with technetium-99m in its reduced state to form a technetium-99m D-glucaric acid complex without the formation of significant technetium colloids. Upon contact with a sulfhydryl containing antibody or antibody fragment, substantially quantitative transfer of technetium-99m from the complex to the protein is achieved rapidly and under mild conditions.

Reducing Agents

Reducing agents for use in the method of this invention are physiologically acceptable for reducing technetium-99m from its oxidized state to the IV or V oxidization state or for reducing rhenium from its oxidized state. Examples of preferred reducing agents which can be used in the method are stannous chloride, stannous fluoride, stannous tartarate, metabisulfite, sodium dithionite and sodium borohydride; the most preferred agents are stannous reducing agents especially stannous chloride.

Radioistopes

The source of technetium-99m in an oxidized state should preferably be water soluble. Preferred sources are alkali and alkaline earth metal pertechnetate ($TcO_4^-$). The technetium-99m is most preferably obtained in the form of fresh sodium pertechnetate from a sterile technetium-99m generator (e.g., from a conventional $^{99}Mo/^{99m}Tc$ generator). Any other source of physiologically acceptable technetium-99m, however, may be used.

Rhenium radioisotopes (the isotopes 186, 188, 189 and 191) in the form of perrhenate salts can be produced by suitable reactor technology or made by a suitable generator. The perrhenate salts are stable, soluble salts and behave similarly to pertechnetate. Perrhenate requires a slightly greater reduction potential to reduce, and tends to return to perrhenate in the presence of oxygen more readily than perteohnetate. For this reason, different conditions may be required to reduce and stabilize rhenium in its reduced state. These can be ascertained empirically by a person of ordinary skill in the art.

Reaction Conditions

The amount of reducing agent is the amount necessary to reduce the Tc or Re to provide for its binding to the coupling agent in a reduced state. In a preferred mode, stannous chloride ($SnCl_2$) is the reducing agent and can range from about 1 to about 1,000 $\mu g/mL$ preferably about 30 to about 500 $\mu g/mL$. In preferred embodiments, D-glucaric acid is present as a transfer ligand, and the amount of D-glucaric acid (as potassium D-glucarate) can range from about 0.5 mg/mL up to the amount maximally soluble in the medium. Preferred amounts of D-glucaric acid range from about 3 to about 15 mg/mL. The amount of antibody (or fragment) can range from about 0.01 to about 30 mg/mL preferably about .17 to about 1.5 mg/mL. Finally, technetium-99m in the form of pertechnetate can be in amounts used up to about 500 mCi/mL preferably about 1 to about 50 mCi/mL. The amount of mCi per mg of antibody or peptide is preferably about 3 to about 150.

The reaction between the above described antibody mixture and the metal ion is preferably carried out in an aqueous solution at a pH at which the protein is stable. By "stable", it is meant that the protein remains soluble and retains its biological activity. Normally, the pH for the reaction will be a pH from about 5 to about 9, the preferred pH being about 6 to about 8. The metal ion or metal ion transfer chelate complex and the antibody are incubated, preferably at a temperature from about 20° C. to about 60° C., most preferably from about 20° C. to about 37° C., for a sufficient amount of time to allow for complexation of the 0 metal ion with the antibody. Generally, less than 30 minutes are sufficient to complete the transfer reaction under these conditions. Times of five to fifteen minutes are routinely achievable. The reaction should also, of course, be carried out under non-oxidizing conditions so that the radioisotope remains in the reduced state.

Kits for Performing the Method

The reagents for performing the present labeling method can be assembled in single vial kit for convenient use on site by the clinician. In one embodiment, the kit contains one vial (sealed and sterile) containing an antibody, antibody fragment, or peptide covalently bound to a coupling agent containing a sulfhydryl group, a reducing agent (preferably stannous ions) and a water soluble ligand (preferably D-glucaric acid or a salt thereof). The kits are designed to contain the appropriate antibody, antibody fragment(s), or peptide for any particular immunodiagnostic or immunotherapeutic procedure (some of which are discussed below).

As used herein, the term "vial" refers to any type of reaction vessel and is not intended to be limiting in any way. These kits can be used when technetium-99m or rhenium radioisotope is provided by the user. Preferably, a sealable reaction vial is used which has means for the introduction and withdrawal of reagent under sterile or semi-sterile conditions. A vial which contains a port for syringe injection is preferred.

The reagents in the kit can be provided in aqueous, frozen or lyophilized form. Lyophilized preparations can be diluted with aqueous medium upon use. The amount of reagents in each vial can vary according to the chosen parameters of the method (see above under Reaction Conditions). The labeling procedure can be performed simply by adding the radioisotope (for example, in the form of aqueous sodium pertechnetate) to the vial containing the antibody or antibody fragment, reducing agent and, in a preferred embodiment, water soluble ligand. The contents of the vial are then mixed and incubated for a time sufficient to effect labeling of the antibody, antibody fragment, or peptide. The duration and condition of incubation are not critical, but incubation is preferably conducted for a period of from about one to sixty minutes, more preferably from about five to thirty minutes. The radiolabeled antibody, antibody fragment, or peptide can then be withdrawn from the vial. No separation or purification is required, and the labeled protein may therefore be used immediately.

Use of the Labeled Antibodies or Peptides in Diagnostics

Technetium-99m labeled antibodies, antibody fragments, or peptides can be used in scintigraphy. One important use is in the imaging of tumors. As mentioned, antibody fragments are preferred for most immunoscintigraphic techniques. Labeled ligand modified Fab' fragments of tumor specific antibodies can be prepared and used to image primary or secondary tumors. In general, the technetium-99m labeled antibody fragment is prepared by combining an aqueous antibody mixture of a coupling agent-modified Fab' fragment specific for the tumor, a reducing agent, and a water soluble transfer ligand with $^{99m}$Tc (usually in the form of pertechnetate).

The labeled coupling agent-modified Fab' fragment can then be injected parenterally (preferably intravenously) into a subject. After injection, sufficient time is allowed for the labeled Fab' fragment to accumulate at the site of the tumor. The subject is then scanned with a gamma camera to detect the gamma emission of the technetium-99m and to thereby obtain an image of the tumor. In this way the tumor can be localized and its size can be determined.

Tumor specific antibody fragments for use in these procedures can be derived from anticolorectal cancer antibody, antilung cancer antibody, antiovarian cancer antibody, antibreast cancer antibody, and antiprostate cancer antibody. Some specific examples of tumor specific antibodies which can be labeled by the method of this invention and used to image tumors are the monoclonal antibodies 17-1A and 19-9 (gastrointestinal), CA 125 (ovarian) and 103D2 (breast).

Antibodies labeled by the method of this invention can be used to label myocardial infarcts. The imaging of myocardial infarcts to determine their size and location is described by Haber, U.S. Pat. No. 4,421,735, the disclosure of which is incorporated herein by reference. In brief, employing the labelling method of this invention, an image of a myocardial infarct in a subject can be obtained by first preparing a $^{99m}$Tc labeled myosin specific coupling agent-modified Fab' fragment by combining an aqueous mixture of a myosin specific coupling agent-modified Fab' fragment, a reducing agent and, preferably, a water soluble transfer ligand with [Tc-99m]pertechnetate. The labeled myosin specific fragment is then intravenously injected into a subject (for example, after coronary occlusion). The labeled fragment is allowed to localize at the site of the infarct and an image of the infarct is obtained by scanning the area of the heart with a gamma camera. A preferred antibody for production of labeled myosin specific Fab' fragments is the monoclonal antibody R11D10.

In addition, fibrin specific ligand modified Fab' fragments can be labelled by the procedure of this invention to provide reagents for imaging blood clots. A $^{99m}$Tc labeled fibrin specific coupling agent-modified fragment is prepared by combining an aqueous antibody mixture of a fibrin specific Fab' fragment, a reducing agent and, preferably, a water soluble transfer ligand with $^{99m}$Tc. The $^{99m}$Tc labeled fibrin specific fragment is injected into the subject. After allowing the fragment to localize at the site of the blood clot, the subject is scanned to obtain an image of the clot. Fibrin specific antibodies which are not cross reactive with fibrinogen are the preferred antibodies for this imaging technique. A preferred antibody for production of labeled fibrin specific ligand modified Fab' fragments is the monoclonal antibody T2Gls.

Antibody fragments specific for bacteria can be used in immunoscintigraphic techniques for obtaining an image of a bacterial abscess in a subject. For this purpose, anti-bacterial or anti-macrophage antibody fragments are employed. Antibodies against a common determinant of gram-negative bacteria (e.g., anti-lipid A antibody) can be used to image an abscess caused by a gram-negative micro-organism. The coupling-agent modified antibody fragment labeled with technetium-99m as described above injected into the subject and allowed to localize at the abscess. The subject is then scanned with the photoscanning equipment to obtain an image of the abscess.

TPA, streptokinase, and urokinase are suitable peptides for labelling according to the present invention for use in blood clot imaging.

Use of the Labeled Antibodies or Peptides in Radiotherapy

The use of an antibody or antibody fragment to transport a radiolabel such as technetium-99m to a tumor and so provide a means of imaging the tumor is described above. In a similar fashion, an antibody or fragment may be used to carry a therapeutic radioisotope such as a beta or alpha emitter to a target tumor. The rhenium isotopes Re-186 and Re-188 may be particularly useful when used in this way. The rhenium-labeled antibodies may be prepared using the same methods as are used for the technetium-labeled antibodies and again fragments such as the Fab' fragment may be used. The isotopes Re-186 and Re-188 have an advantage in that they emit gamma rays also and therefore provide a means of externally detecting where the radiometal has distributed.

The invention is further defined by the following example wherein all parts and percentages are by weight and degrees are Celsius unless otherwise stated.

EXPERIMENTAL

Preparation of N-(2-maleimidoethyl)-(2-(3-carboxybenzoylthio)acetyl)glycylglycylglycinamide (Compound X)

a) Preparation of 2-(tert-butyloxycarbonylamino)ethylamine

To a solution of 7.5 g of aminoacetonitrile hydrochloride (81.05 mmoles,, 150 mol%) and 10.0 g of NaHCO$_3$ (119 mmoles, 220 mol%) in 150 mL of water was added 11.9 g of di-tert-butyl dicarbonate (54.4 mmoles). The heterogeneous mixture was stirred vigorously for 16 h at room temperature. The pH was adjusted to 5.0 with 2 N HCl. The solution was extracted with ethyl acetate (2×75 mL) and the extracts dried over Na$_2$SO$_4$. Filtration and removal of solvent by rotary evaporator gave a brown oil. Kugelrohr distillation gave a fraction bp 95°, 0.10 mmHg as a low melting white solid (8.20 g, 52.5 mmoles, 96%), TLC R$_f$ 0.74(EtOAc), R$_f$ 0.61(EtOAc/hexanes 1:1). In a Parr pressure bottle was placed 2.0 g of the above protected nitrile and 75 mL of glacial acetic acid. After the protected nitrile had dissolved, 0.20 g of 5% Pd/C was added and the mixture hydrogenated at 45 psig H$_2$ for 2 h. The mixture was filtered through acid-washed celite, and the acetic acid removed by rotary evaporator (30°, vacuum pump) to give a tan oil. NMR (CDCl$_3$) δ 1.32 (s, 9H), 2.58 (m, 2H), 3.15 (m, 2H).

b) Preparation of N-(2-tert-butyloxycarbonylamino)ethylmaleimide

The crude N-t-BOC-ethylenediamine prepared above (1.2 g) was dissolved in 25 mL of ice cold saturated NaHCO$_3$ and placed in an ice bath. To this solution was added 0.78 g of N-methoxycarbonylmaleimide (5.0 mmoles, 100 mol%). The heterogeneous mixture was stirred vigorously for 20 min at 0°, followed by 1 h at room temperature. Water (50 ml) was added and the mixture extracted with chloroform (2×50 ml). The extracts were dried over Na$_2$SO$_4$, filtered and the solvent removed to give a white solid. This solid was purified by chromatography on silica gel, eluting with an EtOAc/hexanes gradient. NMR (300 MHz, DMSO-d6) δ1.33 (s,9H), 3.05 (m, 2H), 3.42 (m, 2H), 7.01 (s, 2H).

c) Preparation of 2-maleimidoethylamine

The N-t-BOC derivative described above )0.40 g, 1.7 mmoles) was stirred in trifluoroacetic acid (4 mL) for 1 hours. TFA was removed at the vacuum pump to yield an oil which solidified upon trituration with ether. The maleimide was isolated by filtration and dried under vacuum (0.35 g, 83%). NMR (DMSO-d6) δ2.99 (t, 2H), 3.63 (t, 2H), 7.06 (s, 2H), 8.02 (s, 3H).

d) Preparation of (2-(3-tert-butyloxycarbonylbenzoylthio)acetyl)glycyl-glycylglycine A solution of triglycine (0.53 g, 2.8 mmol) and NaHCO3 (0.26 g, 3.0 mmol) in water (10 mL) was cooled in an ice bath and treated with a solution of succinimidyl 3-tertbutyloxycarbonylbenzoylthioacetate (1.1 g, 2.8 mmol) (Fritzberg, A. R., European Patent Application 86100360.6) in THF (10 mL). After stirring at 0° C. for 30 minutes, the mixture was stirred at room temperature for 1 hour. THF was removed under reduced pressure, and the aqueous mixture was acidified to pH 3 with 1 N HCl. The resulting precipitate was collected and recrystallized from aqueous acetone (0.55 g, 42%). NMR (DMSO-d6) δ1.57 (s, 9H), 3.75 (m, 6H), 3.94 (s, 2H), 7.73 (t, 1H), 8.20 (m, 4H), 8.38 (s, 1H), 8.55 (t, 1H).

e) Preparation of N-hydroxysuccinimidyl (2-(3-tert-butyloxycarbonylbenzoylthio)acetyl)glycyl-glycylglycinate A solution of the above tripeptide (300 mg, 0.64 mmol) and N-hydroxysuccinimide (74 mg, 0.64 mmol) in DMF (3 mL) was treated with a solution of DCC (140 mg, 0.70 mmol) in DMF (1 mL). After stirring at room temperature for 4 hours the mixture was kept in the freezer overnight. The precipitated urea was removed by filtration, and DMF was removed at the vacuum pump. The resulting oil gave a precipitate of the active ester from isopropanol (110 mg, 31%). NMR (DMSO-d6) δ1.58 (s, 9H), 2.82 (s, 4H), 3.81 (m, 4H), 3.93 (s, 2H), 4.28 (m, 2H), 7.72 (t, 1H), 8.20 (m, 2H), 8.32 (t, 1H), 8.40 (s, 1H), 8.55 (m, 2H).

f) Preparation of N-(2-maleimidoethyl)-(2-(3-tert-butyloxycarbonylbenzoylthio)acetyl)glycylglycylglycinamide The above active ester (90 mg, 0.16 mmol) in THF (6 mL) was treated with diisopropylethylamine (31 uL, 0.18 mmol) and maleimido-ethylamine (45 mg, 0.18 mmol). After stirring for four hours, the mixture was concentrated and chromatographed (SiO2, CH2Cl2—CH3OH gradient). Fractions containing the product were concentrated and applied to a prep. TLC plate (SiO2, 20% CH3OH/CH2Cl2) to give the pure maleimido amide (18 mg, 19%) as an oil. NMR (CDCl3—CD3OD) δ1.59 (s, 9H), 3.42 (m, 2H), 3.65 (m, 2H), 3.79 (m, 2H), 3.90 (m, 4H), 3.97 (m, 2H), 6.72 (s, 2H), 7.58 (t, 1H), 8.12 (d, 1H), 8.23 (d, 1H), 8.55 (s, 1H).

g) Preparation of N-(2-maleimidoethyl)-(2-(3-carboxybenzoylthio)acetyl)glycylglycylgylcinamide (Compound X)

The t-butyl ester described above (17 mg, 0.03 mmol) was stirred in trifluoroacetic acid (1 mL) for 1 hour. Removal of the TFA at the vacuum pump gave an oil which precipitated from CH3OH to provide Compound X (12 mg, 78%). NMR (CD Cl3—CD3OD) δ3.32 (m, 4H), 3.59 (t, 2H), 3.74 (m, 2H), 3.82 (m, 2H), 3.88 (m, 2H), 6.67 (s, 2H), 7.55 (t, 1H), 7.81 (t, 1H), 7.98 (t, 1H), 8.10 (m, 2H), 8.24 (d, 1H), 8.58 (s, 1H).

h) Coupling of Compound X to Antimyosin Fab'

Antimyosin Fab' (1 mL, 2.6 mg/mL) pH 7.0 in 0.10 M phosphate containing 1 mM EDTA was analyzed for sulfhydryl content. An aliquot (50μL) was removed and diluted to 1 mL with 0.01 M phosphate, pH 8.0. To this was added 50μL of 5 mg/mL 5,5'-dithiobis-(2-nitrobenzoic acid) (DTNB, Ellman's reagent) in 0.10 M phosphate, pH 8.0. The solution was mixed and $A_{412}$ measured after 15 minutes. Equivalents of sulfhydryls were determined from a molar absorption coefficient of 15,600 at 412 nm and a protein molecular weight of 50,000. A value of 3.5 sulfhydryls/mole was determined. The remaining Antimyosin solution was treated with 50 μL of 1.3 mg/70 μL Compound X in DMF (10 eq. Compound X per protein sulfhydryl). The solution was mixed and allowed to stand at room temperature for 1.5 hours. The reaction mixture was purified by Sephadex G-25 (medium) chromatography (1×10 cm), eluting with 0.10 M phosphate containing 1 mM EDTA, pH 7.0. Fractions (1 mL) were collected and analyzed for protein concentration by $A_{280}$. As a chromophore had been added to the protein, $A_{280}$ values gave only qualitative information. Aliquots (50 μL) of the protein containing fractions were analyzed for sulfhydryl content as above. No absorption was found at 412 nm. Fraction 5 had $A_{280}$ 2.24.

i) Deprotection of the S-Benzoyl

A solution of Compound X-Antimyosin conjugate (0.4 mL) was treated with 0.4 mL of 1.0 M H2NOH.HCl in 0.5 M HEPES, pH 7.5 (adjusted with 50% NaOH). The solution was mixed and left at room temperature for 5 minutes. The mixture was purified by Sephadex chromatography as above. Fractions (1 mL) were collected and analyzed for protein concentration and sulfhydryl content as above. Fraction 5 was found to contain 1.4 mg/mL with 2.6 sulfhydryls/mole.

j) Technetium-99m Labeling of Antimyosin Modified with Compound X

A solution of monopotassium glucarate (12 mg) in 0.2 m NaHCO3 (500 μL) was treated with a solution of stannous chloride (100 μg) in 0.1 M acetic acid (40 μL). The resulting solution was added to deprotected Antimyosin-Compound X conjugate (0.5 mg) in 0.1 M phosphate containing 1 mM EDTA, pH 7.0 (360 μL) contained in a 1 dram vial. To the combined solution containing antimyosin-Compound X, glucarate and stannous ion was added a solution of sodium (Tc-99m) pertechnetate solution (140 μL 2.4 mCi) from a Mo-99/Tc-99m generator. The resulting solution was mixed and allowed to stand at room temperature. After 10 minutes, ITLC on Gelman ITLC-SG (0.1 M sodium citrate, pH 5.0 developer) showed labeling was 99% complete. HPLC showed 17% of the radioactivity at $R_t$ 8.6 [F(ab')2] and 83% at $R_t$ 9.6 (Fab'). The immunoreactivity as determined by a myosin column binding assay was 99%. Upon passage through a 0.22 um membrane filter, 94% of the radioactivity was recovered, without a rinse.

Equivalents

Those skilled in the art will recognize, or be able to ascertain using no more than routine experimentation, many equivalents to the specific embodiments of the invention described herein. Such equivalents are intended to be encompassed by the following claims.

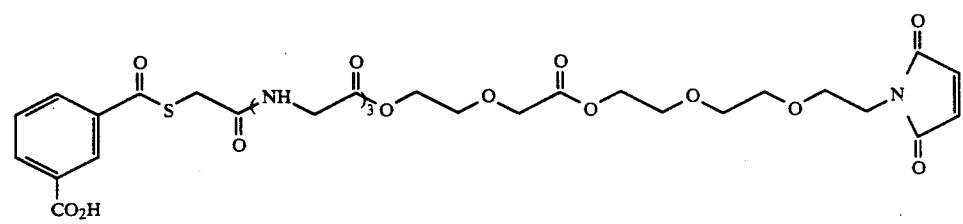

What is claimed is:

1. A one vial method for labeling a protein with a radioisotope selected from Tc-99m, Re-186, Re-188, Re-189 and Re-191, comprising (a) providing a vial containing a mixture comprising said protein having a sulfhydryl containing bisectional coupling agent bound thereto and a reducing agent; and (b) adding to said vial said radioisotope in an oxidized state, wherein said bisectional coupling agent is selected from compounds of the formula

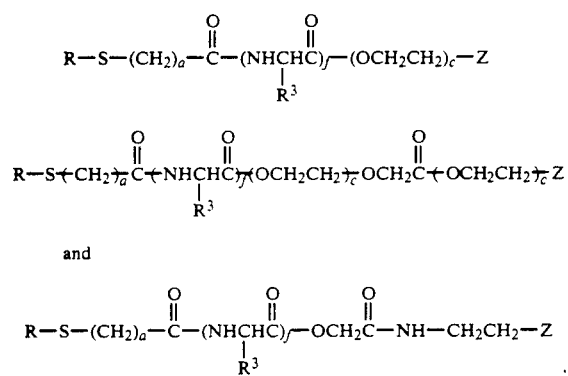

and where
a is an integer from 1 to 3 inclusive;
c is an integer from 1 to 7 inclusive;
f is an integer from 3 to 6 inclusive;
R is selected from the group consisting of $R_1CO-$ and $R_1S-$;
$R_1$ is selected from the group consisting of optionally substituted lower alkyl and optionally substituted aryl;
$R_3$ is selected from the group consisting of hydrogen, optionally substituted lower alkyl, and optionally substituted aryl; and
Z is selected from the group consisting of $ClCH_2CONH-$, $BrCH_2CONH-$, $ICH_2COHN-$ and N-substituted maleimido.

2. The method of claim 1 wherein said radioisotope is Tc-99m.

3. The method of claim 1 wherein said protein is an antibody or an antibody fragment.

4. The method of claim 2 wherein said protein is a Fab' fragment.

5. The method of claim 1 wherein said coupling agent is bound to said protein at a sulfhydryl site on said protein.

6. The method of claim 1 in which said mixture further comprises a water-soluble transfer ligand.

7. The method of claim 6 in which said water-soluble transfer ligand is one of the formula:

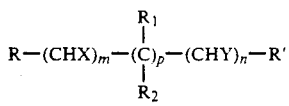

where
X and Y are OH or $NH_2$;
R and R' are independently H, COOH, or $CH_2OH$ or R and R' taken together can form a ring or bi- or multidentate ligand;
m and n are 0–10, such that m+n is at least 2;
$R_1$ and $R_2$ are independently H, optionally substituted lower alkyl, aryl and lower alkylaryl; and
p is 0 or 1 provided that, when p is 1, m and n independently are at least 1.

8. The method of claim 7 in which said water-soluble transfer ligand is one of the formula:

$$R-(CHOH)_n-R'$$

where
R and R' are COOH or $CH_2OH$, and n=2–10.

9. The method of claim 8 in which said ligand is D-glucaric acid or a salt thereof.

10. The method of claim 1 in which said reducing agent is a stannous reducing agent.

11. The method of claim 1 in which said radioisotope is Tc-99m, said protein is a Fab' fragment, said coupling agent is bound to said Fab' fragment at a sulfhydryl site on said fragment, said reducing agent is a stannous reducing agent, and said mixture further comprises D-glucaric acid.

12. The method of claim 11 in which said mixture comprises about 1 to 1000 ug/mL stannous chloride, about 3 to 15 mg/L D-glucaric acid, and about 0.01 to 30 mg/mL Fab' fragment.

13. The method of claim 12 in which said radioisotope is added to said mixture in the form of an aqueous solution of Tc-m pertechnetate of about 1 to 50 mCi/mL.

14. The method of claim 1 in which said radioisotope is selected from Re-186 and Re-188, said protein is a Fab' fragment, said coupling agent is bound to said Fab' fragment at a sulfhydryl site on said fragment, said reducing agent is a stannous reducing agent, and said mixture further comprises D-glucaric acid.

15. The method o claim 1 in which said protein mixture is lyophilized and said radioisotope is added in the form of an aqueous solution.

16. The method of claim 1 wherein said bifunctional coupling agent has the formula

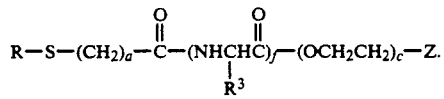

17. The method of claim 1 where said bifunctional coupling agent of the formula

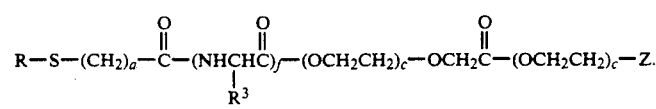

18. The method of claim 1 where said bifunctional coupling agent has the formula

R—S(CH₂)ₐ̄C(O)—NHCHC(O)ᵢ—OCH₂C(O)—NH—CH₂CH₂—Z.
             |
             R³

19. The method of claim 1 where said bifunctional coupling agent has the formula

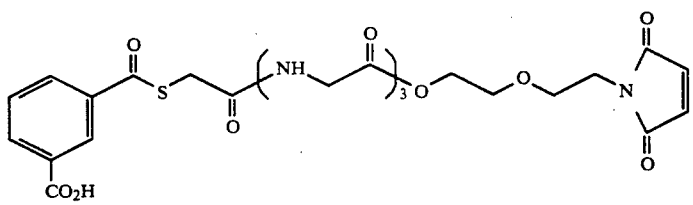

20. The method of claim 1 where said bifunctional coupling agent has the formula

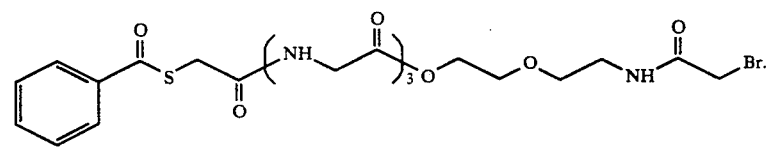

21. The method of claim 1 where said bifunctional coupling agent has the formula

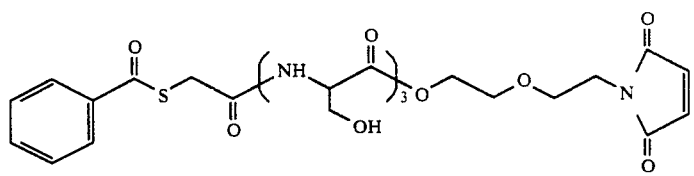

22. The method of claim 1 where said bifunctional coupling agent has the formula

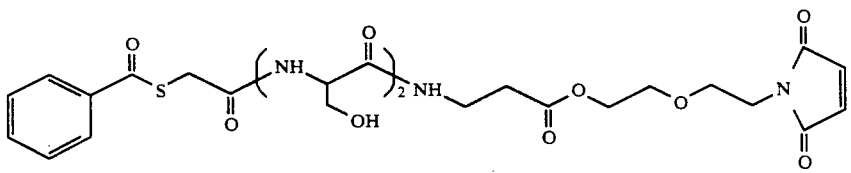

23. The method of claim 1 where said bifunctional coupling agent has the formula

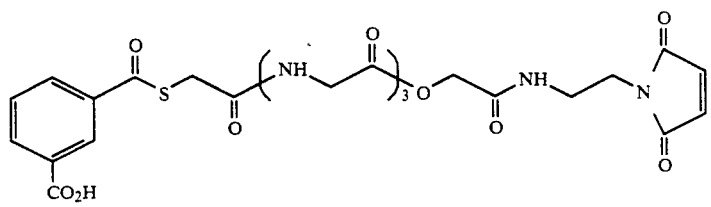

24. The method of claim 1 where said bifunctional coupling agent has the formula

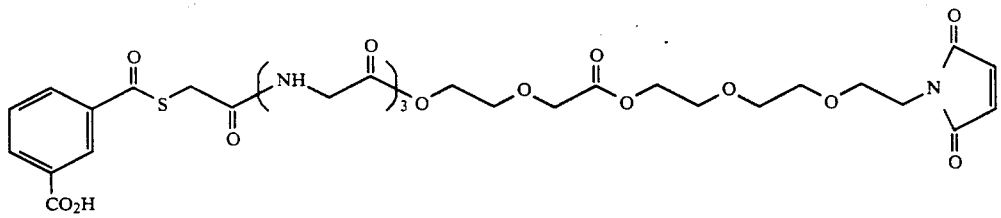

25. The method of claim 1 where said bifunctional coupling agent has the formula

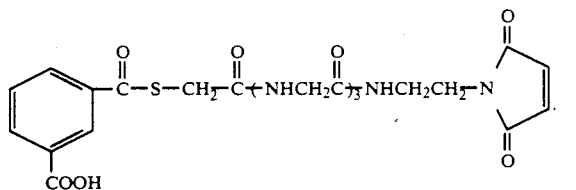

26. A one vial kit for labeling a protein with a radioisotope selected from Tc-99m, Re-186, Re-188, Re-189 and Re-191, comprising a vial containing a mixture comprising said protein having a sulfhydryl containing bifunctional coupling agent bound thereto and a reducing agent, wherein said bifunctional coupling agent is selected from compounds of the formula

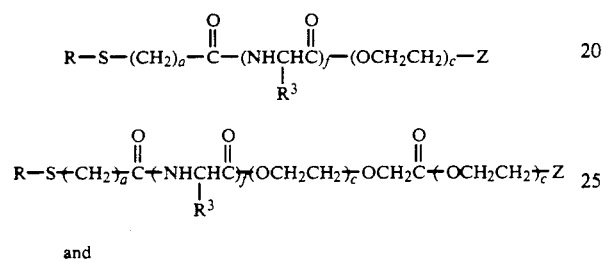

and

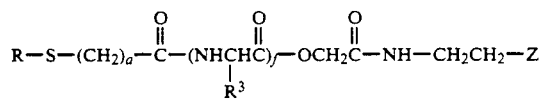

where
- a is an integer from 1 to 3 inclusive;
- c is an integer from 1 to 7 inclusive;
- f is an integer from 3 to 6 inclusive;
- R is selected from the group consisting of $R_1CO$— and $R_1R$—;
- $R_1$ is selected from the group consisting of optionally substituted lower alkyl and optionally substituted aryl;
- $R_3$ is selected from the group consisting of hydrogen, optionally substituted lower alkyl, and optionally substituted aryl; and
- Z is selected from the group consisting of $ClCH_2CONH$—, $BrCH_2CONH$—, $ICH_2CPNH$ and N-substituted maleimido.

27. The kit of claim 26 wherein said protein is an antibody or an antibody fragment.

28. The kit of claim 27 wherein said protein is a Fab' fragment.

29. The kit of claim 26 wherein said coupling agent is bound to said protein at a sulfhydryl site on said protein.

30. The kit of claim 26 in which said mixture further comprises a water-soluble transfer ligand.

31. The kit of claim 30 in which said water-soluble transfer ligand is one of the formula:

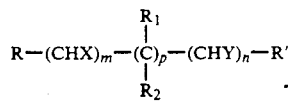

where
- X and Y are OH or $NH_2$;
- R and R' are independently H, COOH, or $CH_2OH$ or R and R' taken together can form a ring or bi- or multidentate ligand;
- m and n are 0–10, such that m+n is at least 2;
- $R_1$ and $R_2$ are independently H, optionally substituted lower alkyl, aryl and lower alkylaryl; and
- p is 0 or 1 provided that, when p is 1, m and n independently are at least 1.

32. The kit of claim 31 in which said water-soluble transfer ligand is one of the formula:

where
R and R' are COOH or $CH_2OH$, and n=2–10.

33. The kit of claim 32 in which said ligand is D-glucaric acid or a salt thereof.

34. The kit of claim 26 in which said reducing agent is a stannous reducing agent.

35. The kit of claim 26 in which said mixture comprises about 1 to 1000 ug/mL stannous chloride, about 3 to 15 mg/L D-glucaric acid, and about 0.01 to 30 mg/mL Fab' fragment.

36. The kit of claim 35 in which said protein mixture is lyophilized.

37. The kit of claim 26 where said bifunctional coupling agent has the formula

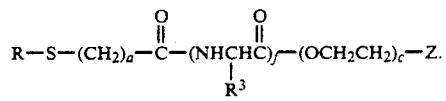

38. The kit of claim 26 where said bifunctional coupling agent of the formula

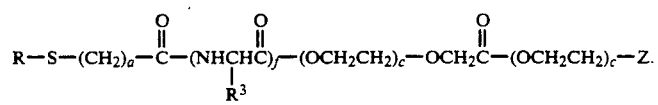

39. The kit of claim 26 where said bifunctional coupling agent has the formula

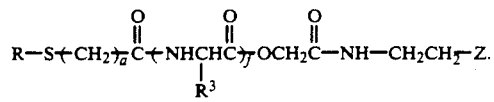

40. The kit of claim 26 where said bifunctional coupling agent has the formula

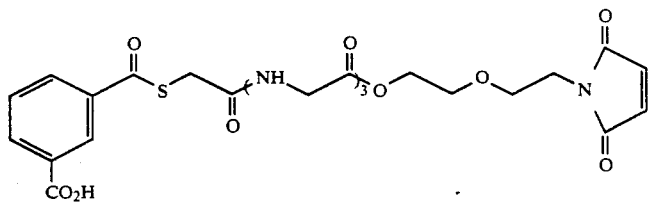

41. The kit of claim 26 where said bifunctional coupling agent has the formula

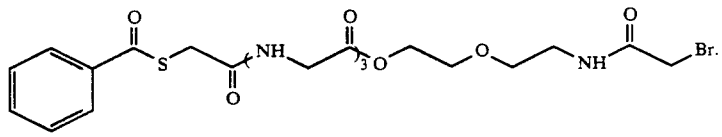

42. The kit of claim 26 where said bifunctional coupling agent has the formula

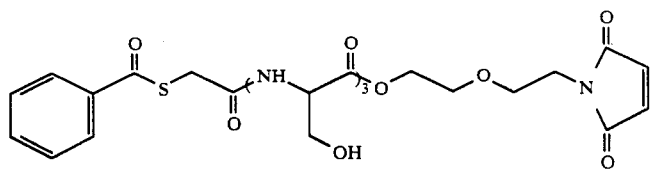

43. The kit of claim 26 where said bifunctional coupling agent has the formula

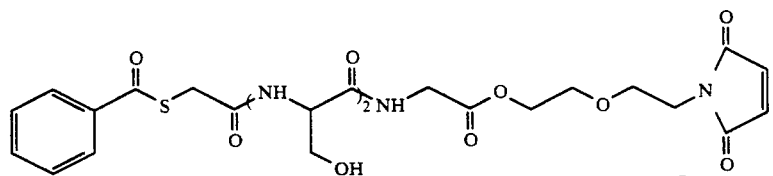

44. The kit of claim 26 where said bifunctional coupling agent has the formula

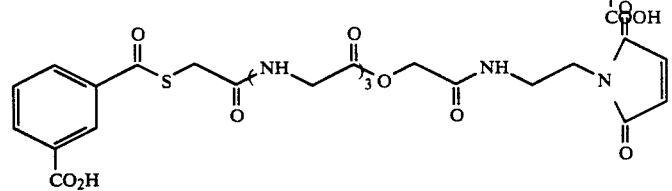

45. The kit of claim 26 where said bifunctional coupling agent has the formula

46. The kit of claim 26 where said bifunctional coupling agent has the formula

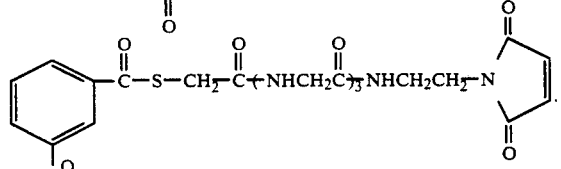

* * * * *